United States Patent [19]

Oppenlaender et al.

[11] 4,189,445

[45] Feb. 19, 1980

[54] SURFACE-ACTIVE PHENOLIC DERIVATIVES

[75] Inventors: Knut Oppenlaender, Ludwigshafen; Karl Stork, Lampertheim; Ewald Daubach; Manfred Herrmann, both of Ludwigshafen, all of Fed. Rep. of Germany

[73] Assignee: BASF Aktiengesellschaft, Ludwigshafen, Fed. Rep. of Germany

[21] Appl. No.: 948,349

[22] Filed: Oct. 4, 1978

[30] Foreign Application Priority Data

Oct. 8, 1977 [DE] Fed. Rep. of Germany ....... 2745449
Nov. 18, 1977 [DE] Fed. Rep. of Germany ....... 2751519

[51] Int. Cl.$^2$ .................... C07C 43/20; C07C 141/14
[52] U.S. Cl. ................................ 260/458 C; 252/353; 568/609
[58] Field of Search .................... 260/457, 458 C; 568/609

[56] References Cited

U.S. PATENT DOCUMENTS

| | | | |
|---|---|---|---|
| 2,504,064 | 4/1950 | Bock et al. | 568/609 |
| 2,630,457 | 3/1953 | Hansen et al. | 568/609 |
| 2,930,778 | 3/1960 | Boettner | 568/609 |
| 3,265,722 | 8/1966 | Dudley | 260/458 C |
| 3,313,838 | 4/1967 | Rozzi | 260/458 C |
| 3,359,306 | 12/1967 | Farnham | 260/458 C |
| 3,528,986 | 9/1970 | Pala | 260/457 |
| 3,699,173 | 10/1972 | Osberg et al. | 568/609 |
| 3,875,202 | 4/1975 | Steckler | 260/458 C |
| 3,919,429 | 11/1975 | Grossmann et al. | 260/458 C |
| 3,925,483 | 12/1975 | Buzzolini et al. | 260/457 |
| 4,137,251 | 1/1979 | Berger | 260/458 C |

FOREIGN PATENT DOCUMENTS

| | | | |
|---|---|---|---|
| 36-23491 | 12/1961 | Japan | 568/609 |
| 47-20074 | 2/1971 | Japan | 568/609 |
| 1054298 | 1/1967 | United Kingdom | 568/609 |

*Primary Examiner*—Norman Morgenstern
*Attorney, Agent, or Firm*—Oblon, Fisher, Spivak, McClelland & Maier

[57] ABSTRACT

Oxyalkylated bisphenols are obtained from 2,2-(p,p'-bishydroxydiphenyl)-propane and styrene in the presence of an acid catalyst and are then oxyalkylated, after which they may or may not be sulfated.

6 Claims, No Drawings

SURFACE-ACTIVE PHENOLIC DERIVATIVES

BACKGROUND OF THE INVENTION

1. Field of the Invention

The present invention relates to novel surfactants which in some cases are also dispersants.

SUMMARY OF THE INVENTION

The novel compounds have the formula I

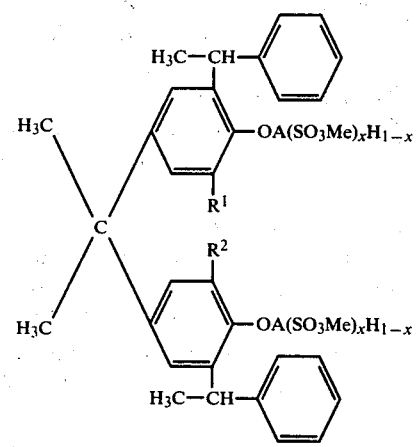

where $R^1$ and $R^2$ are identical or different and each is hydrogen or

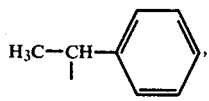

Me is an alkali metal cation or a substituted or unsubstituted ammonium cation, x is from 0 to 1 and A is a radical of a polymer of ethylene oxide or of propylene oxide, or of a block polymer or copolymer of ethylene oxide with propylene oxide, the radical containing a total of from 5 to 250 alkylene oxide units.

Preferably, $R^1$ and $R^2$ are each

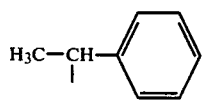

A is preferably a propylene oxide/ethylene oxide block polymer radical.

In the preparation of the compounds, a phenol of the formula II

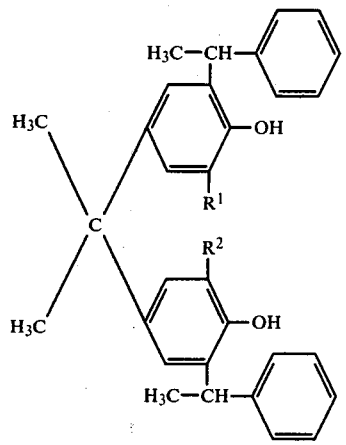

where $R^1$ and $R^2$ are defined as in formula I, is reacted with ethylene oxide, propylene oxide or a mixture of these, or with propylene oxide followed by ethylene oxide, in the conventional manner, using such amounts that from 5 to 250 alkylene oxide units are bonded per phenolic hydroxyl, and the resulting oxyalkylation product is then reacted further with x moles of a sulfating agent per free hydroxyl group, x being as defined in formula I.

The starting phenols are prepared in the conventional manner by reacting 2,2-(p,p'-bishydroxydiphenyl)-propane ("bisphenol A") with from 2 to 4 moles of styrene in the presence of an acid catalyst. Advantageously, the procedure followed is that less than the appropriate amount of styrene is heated to about 30°–70° C. and the bisphenol together with a catalyst is introduced, whereupon the temperature rises to 100°–150° C. The remainder of the styrene is then added in the course of from 1½ to 5 hours and the reaction is allowed to continue for some time thereafter.

In principle, the entire charge can be reacted at once, but this is not always feasible, especially in the case of sizable batches, because of the difficulty presented by the amount of heat to be removed as a result of the exothermicity.

The acid catalyst, which is present in an amount of from about 0.5 to 1% by weight, based on styrene employed, is advantageously, for example, sulfuric acid, p-toluenesulfonic acid or $AlCl_3$ or some other Lewis acid.

The reaction product obtained, which has the formula II, is then reacted with such an amount of ethylene oxide and/or propylene oxide per phenolic OH group as to bond from 5 to 250 alkylene oxide units to each such OH group. This reaction can be carried out in various ways.

The reaction can be exclusively an oxyethylation, in which case preferably from 10 to 250 moles of ethylene oxide are reacted per OH group, though this amount also depends on the meanings of $R^1$ and $R^2$ (with the phenylethyl radicals conferring hydrophobic character).

It is however also possible to form an adduct first with propylene oxide and then with ethylene oxide, the amounts used being such that the total of bonded alkylene oxide units does not exceed 250. Amongst this total, there are preferably up to 125 propylene oxide units.

Finally, the adduct formation can also be carried out with propylene oxide alone or with ethylene oxide and propylene oxide in succession or mixed with one another, provided that the total number of alkylene oxide units is as defined above.

Preferably, the product obtained with 4 moles of styrene per mole of bisphenol A is subjected to adduct formation with propylene oxide and ethylene oxide in succession, or with ethylene oxide alone.

The oxyalkylation of phenolic hydroxyl groups is a reaction which has been known for a long time and hence no longer requires special explanation.

The reaction takes place in an alkaline medium, for example in the presence of an alkali metal hydroxide, eg. NaOH or KOH, at from 80° to 150° C., under a pressure of from 2 to 10 bar, and gives compounds of the formula I where $x=0$.

The oxyalkylation products may then be reacted with a sulfating agent, preferably chlorosulfonic acid or sulfur trioxide, the sulfating agent being employed in an amount such that either all or only some of the free OH groups are sulfated. In the latter case, a mixture of compounds of the formula I containing free hydroxyl groups and sulfated hydroxyl groups is obtained.

Finally, the sulfuric acid half-esters formed are neutralized. This is done in the conventional manner with an alkali metal hydroxide, eg. NaOH or KOH, ammonia or an amine, eg. triethylamine, triisopropylamine, monoethanolamine, diethanolamine, triethanolamine, monoisopropanolamine, diisopropanolamine or triisopropanolamine.

Both the non-sulfated and the neutralized sulfated compounds of the formula I are excellent surfactants of which some, especially those defined in claims 2 and 3, exhibit an excellent dispersing action for a variety of materials. A particular use of the compounds is described in detail in our co-pending German Application P 27 45 499.5.

The Examples which follow illustrate the invention. Parts are by weight, unless stated otherwise, and bear the same relation to parts by volume as that of the kilogram to the liter.

EXAMPLES (a) Preparation of the phenol derivative of the formula II 312 parts ($\triangleq 3$ molar parts) of styrene are introduced into a round flask, having a capacity of 4,000 parts by volume and equipped with a stirrer, dropping funnel, thermometer and reflux condenser, and are heated to 50° C. 684 parts ($\triangleq 3$ molar parts) of 2,2-(p,p'-bishydroxydiphenyl)-propane are introduced at this temperature and 9.7 parts of anhydrous p-toluenesulfonic acid are added to the suspension. After a short time, an exothermic reaction occurs and the temperature of the reaction solution rises to about 120°–140° C. A clear oil results. A further 936 parts ( 9 molar parts) of styrene are added to this reaction mixture in the course of 3 hours at 120°–140° C. To complete the reaction, the mixture is stirred for another hour at 120°–140 C. The product, which is very viscous at room temperature, is poured out at 70°–90° C.

Color of product: reddish brown.
Yield: 1,896 g.

(b) Oxyalkylation (b1) 1,896 parts (=3 molar parts) of the reaction product obtained as described in (a), and 19 g of potassium hydroxide powder are introduced into an autoclave and 870 parts of propylene oxide (15 molar parts) are injected in portions, at a rate such that the pressure does not exceed 3 bar, whilst stirring at 120° C.

13,200 parts (300 molar parts) of ethylene oxide are then injected in the same way at the same temperature.

The reaction product is run out of the autoclave whilst warm and solidifies, on cooling, to a colorless mass.

Melting point about 52° C.

If n in formula I is 0, the reaction product obtained as described in (a) is reacted with ethylene oxide only, under the same conditions as above, at 120° C.

(b2) 1,896 parts (=3 molar parts) of the product prepared as described in a) are mixed with 19 g of potassium hydroxide powder in an autoclave and 13,200 parts (=300 molar parts) of ethylene oxide are injected in portions, at a rate such that the pressure does not exceed 3 bar, whilst stirring at 120° C.

The oxyethylation product (15,115 parts) is run out whilst still warm and solidifies to a colorless mass.

Melting point about 50° C.

(c) Preparation of the sulfuric acid half-esters 15,115 parts (=3 molar parts) of the ethylene oxide adduct obtained as described in (b2) are melted, the melt is cooled to 50°–60° C., and at this temperature 349.5 g of chlorosulfonic acid are added dropwise in the course of 10 minutes. To complete the reaction, stirring is continued for 30 minutes at 50°–70° C.

The reaction mixture is then neutralized with about 50% strength aqueous sodium hydroxide solution at below 70° C. (ph 6-7). The product can be poured out at 60°–70° C. and solidifies on cooling.

Melting point about 50° C.
Yield: 15,428 parts.

The reaction can also be carried out in the same manner with sulfur trioxide.

Further water-soluble surfactants (b) and (c) were prepared by a similar method. Details of these are shown in the Table which follows.

The surfactants are characterized by listing the phenol on which they are based, the amount of propylene oxide and ethylene oxide used per mole of phenol to form the adduct, and the amount of chlorosulfonic acid used per mole of adduct.

TABLE

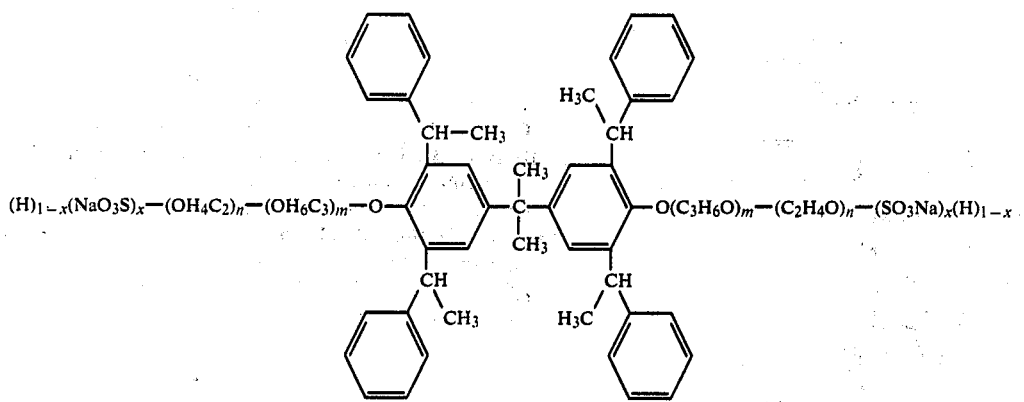

| water-soluble surfactant Example No. | moles of propylene oxide/ mole of phenol | $\bar{m}$ | moles of ethylene oxide/ mole of phenol | $\bar{n}$ | moles of chlorosulfonic acid/ mole of adduct | $\bar{x}$ | melting point (°C.) |
|---|---|---|---|---|---|---|---|
| 1 | 0 | 0 | 75 | 37.5 | 0 | 0 | 48 |
| 2 | 0 | 0 | 100 | 50 | 0 | 0 | 50 |
| 3 | 0 | 0 | 125 | 62.5 | 0 | 0 | 52 |
| 4 | 0 | 0 | 150 | 75 | 0 | 0 | 54 |
| 5 | 0 | 0 | 200 | 100 | 0 | 0 | 56 |
| 6 | 0 | 0 | 300 | 150 | 0 | 0 | 58 |
| 7 | 0 | 0 | 500 | 250 | 0 | 0 | 60 |
| 8 | 5 | 2.5 | 100 | 50 | 0 | 0 | 52 |
| 9 | 100 | 50 | 150 | 75 | 0 | 0 | viscous |
| 10 | 100 | 50 | 200 | 100 | 0 | 0 | viscous |
| 11 | 200 | 100 | 250 | 125 | 0 | 0 | oil |
| 12 | 0 | 0 | 75 | 37.5 | 2 | 1.0 | 48 |
| 13 | 0 | 0 | 100 | 50 | 1 | 0.5 | 50 |
| 14 | 0 | 0 | 200 | 100 | 1 | 0.5 | 57 |
| 15 | 0 | 0 | 125 | 62.5 | 2 | 1.0 | 52 |
| 16 | 0 | 0 | 300 | 150 | 1 | 0.5 | 58 |
| 17 | 0 | 0 | 500 | 250 | 1 | 0.5 | 60 |
| 18 | 5 | 2.5 | 150 | 75 | 2 | 1.0 | 54 |
| 19 | 100 | 50 | 100 | 50 | 2 | 1.0 | oil |
| 20 | 100 | 50 | 150 | 75 | 2 | 1.0 | oil |
| 21 | 100 | 50 | 200 | 100 | 2 | 1.0 | viscous |
| 22 | 200 | 100 | 250 | 125 | 2 | 1.0 | viscous |
| 23 | 1.0 | 0.5 | 100 | 50.0 | 1 | 0.5 | 52 |
| 24 | 2.0 | 1.0 | 100 | 50 | 1 | 0.5 | 52 |

What is claimed as new and intended to be covered by Letters Patent is:

1. A compound of the formula I

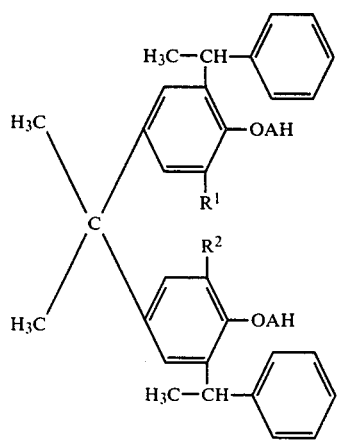

(I)

where $R^1$ and $R^2$ are identical or different and each is hydrogen or

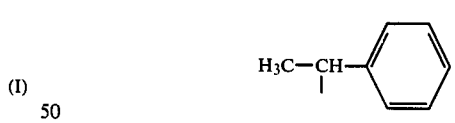

and A is a radical of a polymer of ethylene oxide or of propylene oxide, or of a block polymer or copolymer of ethylene oxide with propylene oxide, the radical containing a total of from 5 to 250 alkylene oxide units.

2. A compound of the formula I as claimed in claim 1, where $R^1$ and $R^2$ are each

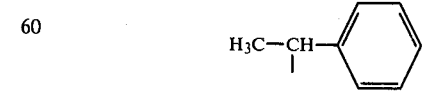

3. A compound of the formula I as claimed in any of claims 1 or 2, where A is a radical of the formula $-(C_3H_6O)_m(C_2H_4O)_n$-, m being from 0 to 125 and n from 10 to 250.

4. A compound of the formula II

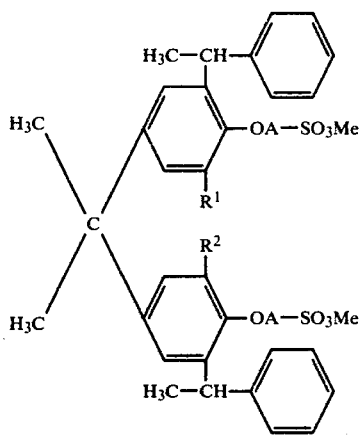

where R¹ and R² are identical or different and each is hydrogen or

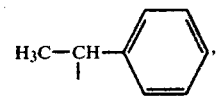

Me is an alkali metal cation or a substituted or unsubstituted ammonium cation, and A is a radical of a polymer of ethylene oxide or of propylene oxide, or of a block polymer or copolymer of ethylene oxide with propylene oxide, the radical containing a total of from 5 to 250 alkylene oxide units.

5. A compound of formula II as claimed in claim 4 wherein R¹ and R² are each

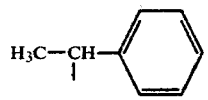

6. A compound of the formula II as claimed in any of claims 4 or 5 wherein A is a radical of the formula -$(C_3H_6O)_m(C_2H_4O)_n$-, m being from 0 to 125 and n from 10 to 250.

* * * * *